(12) United States Patent
Kong (10) Patent No.: US 7,524,872 B2
(45) Date of Patent: *Apr. 28, 2009

(54) METHOD AND COMPOSITION FOR TREATING CANCER USING CELLULAR ORGANELLE CRYSTALLIZING AGENTS

(76) Inventor: Qingzhong Kong, Biology Building, Room 128 Sbandong University, East Campus, Jinan, Shandong Province 250100 (CN)

( * ) Notice: Subject to any disclaimer, the term of this patent is extended or adjusted under 35 U.S.C. 154(b) by 784 days.

This patent is subject to a terminal disclaimer.

(21) Appl. No.: 11/004,513

(22) Filed: Dec. 3, 2004

(65) Prior Publication Data

US 2006/0286170 A1  Dec. 21, 2006

Related U.S. Application Data

(63) Continuation-in-part of application No. 10/096,156, filed on Mar. 11, 2002, now Pat. No. 6,864,272, which is a continuation of application No. 09/663,559, filed on Sep. 15, 2000, now Pat. No. 6,376,525.

(51) Int. Cl.
| | |
|---|---|
| A61K 31/41 | (2006.01) |
| A61K 31/425 | (2006.01) |
| C07D 257/04 | (2006.01) |
| C07D 257/10 | (2006.01) |
| C12Q 1/26 | (2006.01) |
| C12Q 1/32 | (2006.01) |

(52) U.S. Cl. .................. 514/340; 514/382; 514/370; 514/44; 548/250; 435/25; 435/26; 435/375; 435/455

(58) Field of Classification Search .......... 514/382, 514/340
See application file for complete search history.

(56) References Cited

U.S. PATENT DOCUMENTS

| | | | |
|---|---|---|---|
| 3,418,212 A | 12/1968 | Fitzgibbons | |
| 4,001,089 A | 1/1977 | Stavropoulos et al. | |
| 4,152,116 A | 5/1979 | Deneke et al. | |
| 4,565,783 A | 1/1986 | Hansen et al. | |
| 5,225,328 A | 7/1993 | Chang | |
| 5,278,047 A | 1/1994 | Lilja et al. | |
| 5,416,064 A * | 5/1995 | Chari et al. | 514/229.5 |
| 5,529,906 A | 6/1996 | Shimizu et al. | |
| 5,626,862 A | 5/1997 | Brem et al. | 424/426 |
| 5,703,110 A | 12/1997 | Naka et al. | 514/396 |
| 5,726,009 A | 3/1998 | Connors et al. | 435/4 |
| 5,736,129 A | 4/1998 | Medenica et al. | 424/85.4 |
| 5,789,417 A | 8/1998 | Boyle et al. | 514/267 |
| 6,368,818 B1 | 4/2002 | Kong | |
| 6,376,525 B1 * | 4/2002 | Kong | 514/382 |
| 6,864,272 B2 * | 3/2005 | Kong | 514/382 |
| 7,102,011 B2 | 9/2006 | Kong | |

OTHER PUBLICATIONS

International Search Report for International (PCT) Patent Application No. PCT/US01/13730, mailed Oct. 20, 2001.
International Preliminary Examination Report fo International (PCT) Patent Application No. PCT/US01/13730, mailed Aug. 6, 2002.
Examiner's First Report for Australian Patent Application No. 2001257383, mailed Jun. 22, 2005.
Examiner's First Report for Australian Patent Application No. 2006225259, mailed Dec. 13, 2007.
Supplementary European Search Report for European Patenet Application No. 01930891.5, mailed Aug. 17, 2007.
Examination Report for European Patent Application No. 01930891.5, mailed Jun. 19, 2008.
Official Action for Canadian Patent Application No. 2,407,112, mailed Aug. 27, 2008.
Official Action for Canadian Patent Application No. 2,407,112, mailed Mar. 21, 2007.
Abe et al., 1999, *Brain Res.*, 830: 146-154.
Abe et al.,(1998), *Neuroscience Res*, 31: 295-305.
Auferheide et al., 1999, *Exp. Toxic Pathol.*, 51: 3-7.
Bakkenist CJ, et al., 1999 *Cancer Res* 59(17): 4219-21.
Bemas T, et al., (1999) *Biochim Biophys Acta*, 12;1451(1): 73-81.
Berridge, M.V. and Tan, A.S. (1993) *Arch Biochem Biophys* 303(2): 474-482.
Brinkley BR, et al., (1998) *Cell Motil Cytoskeleton.* 41(4): 281-8 Review.
Carroll PE, et al., (1999) *Oncogene* 18(11): 1935-44.
Compton, D.A. (1999) *Science* 286: 913-914.
Cross D, et al., (1996) *Exp Cell Res.* 229(2): 378-87.
Dang et al., (1999) *Clinical Cancer Res.* 5:471-474.
Doxsey S, (1998) *Nat Genet.* 20(2): 104-6.

(Continued)

*Primary Examiner*—Andrew D Kosar
*Assistant Examiner*—Shyam Nathan
(74) *Attorney, Agent, or Firm*—Sheridan Ross P.C.

(57) ABSTRACT

This invention provides a method for treating cancer in mammals through cellular-organelle-crystallization-induced-death (herein defined as "Cocid"), a method for treating cancer using cellular organelle and/or cytoskeleton crystallizing agents (e.g. tetrazolium salts and their derivatives), pharmaceutical compositions containing a therapeutically effective amount of organelle and/or cytoskeleton crystallizing agents, and compositions containing organelle and/or cytoskeleton crystallizing agents in combination with a pharmaceutically acceptable carrier, diluent or excipient. The crystallizing agents with or without a pharmaceutically acceptable carrier, diluent or excipient, are used in combination with surgery and/or non-surgical anti-tumor treatments.

8 Claims, 6 Drawing Sheets
(4 of 6 Drawing Sheet(s) Filed in Color)

OTHER PUBLICATIONS

Flory MR. Et al., (2000) *Proc Natl Acad Sci U S A* 23;97(11): 5919-23.
Fry AM, et al., (1998) *J Biol Chem*. 274(23): 16304-10.
Gstaiger M. et al., (1999) *Exp Cell Res* 247(2): 554-62.
Hinchcliffe EH, et al., (1999) *Science* 283(5403): 851-4.
Hsu LC and White RL (1998) *Proc Natl Acad Sci U S A* 95(22): 12983-8.
Keryer G, et al., ( 1999) *Exp Cell Res*. 249(1): 131-46.
Kimura M, et al., (1999) *J Biol Chem* 274(11):7334-40.
Kong Q. et al., (2000) *Medical Hypotheses* 55(1):29-35.
Kong Q. et al., (1998) *J Surg Oncol* 69:76-82.
Kong Q. et al., (1998) *Med. Hypoth*. 51:405-9.
Kong Q. et al., (1997) *J. Surg. Oncol*. 64: 268-273.
Kuo KK, et al., (2000) *Hepatology* 31(1): 59-64.
Leung et al., (1992), *Leuk. Res*., 16(9): 929-935.
Lingle WL, et al., (1998) *Proc Natl Acad Sci U S A*. 95(6): 2950-5.
Liu et al., 1997, *J Neurochem*., 69(2): 581-593.
Masaki et al., (1995) *J. Dermatological Sci*., 10:25-34.
Mayer TU, et al., (1999) *Science* 286(5441): 971-4.
Mussman JG, et al., (2000) *Oncogene* 23;19(13): 1635-46.
Nakadai T, et al., (1999) *J Cell Sci*. 112 ( Pt 9): 1353-64.
Paintrand M. et al., (1992) *J Struct Biol* 108(2): 107-28.
Passalacqua M. et al., (1999) *Biochem J* 337 ( Pt 1): 113-8.
Pihan GA, et al., (1998) *Cancer Res* 58(17): 3974-85.
Salisbury JL, et al., (1999) *J Histochem Cytochem*. 47(10): 1265-74.
Sato N. et al., (1999) *Clin Cancer Res*. 5(5): 963-70.
Shan B. et al., (1999) *Proc Natl Acad Sci U S A* 96(10): 5686-5691.
Tanaka T, et al., (1999) *Cancer Res* 59(9): 2041-4.
Verma et al., 1997, *Nature*, 389: 239-242.
Weber RG, et al., (1998) *Cytogenet Cell Genet* 83(3-4): 266-9.
Weber et al., 1999, *Histochem. J*., 31: 293-301.
Xu X, et al., (1999) *Mol Cell* 3(3): 389-95.
Zhou H. et al., (1998) *Nat Genet*. 20(2): 189-93.
Zimmerman W. et al., (1999) *Curr Opin Cell Biol* 11(1): 122-8.
Wang, H., Shah, V., Lanks, K.W., Use of Oxidizing Dyes in Combination with 2-Cyanocinnamic Acid to Enhance Hyperthermic Cytotoxicity in L929 Cells, Cancer Research, 47:3341-43, (Jul. 1, 1987).
Chauhan, P.S., Tetrazolium Salts Adrenergic Blockade by Blue Tetrazolium, Experientia, 5(25):511-12 (1969).
Supplementary Partial European Search Report for European Patent Application No. 01930891.5-2107 based on PCT Application No. PCT/US0113730.

* cited by examiner

METHOD AND COMPOSITION FOR TREATING CANCER USING CELLULAR ORGANELLE CRYSTALLIZING AGENTS

CROSS REFERENCE TO RELATED APPLICATION

This application is a continuation-in-part of U.S. patent application Ser. No. 10/096,156, filed Mar. 11, 2002 now U.S. Pat. No. 6,864,272, which is a continuation of U.S. patent application Ser. No. 09/663,559, now U.S. Pat. No. 6,376,525, filed Sep. 15, 2000, both of which are incorporated herein, in their entirety, by this reference.

FIELD OF THE INVENTION

The present invention relates to the use of cellular organelle crystallizing agents to treat cancer cells, to pharmaceutical compositions containing cellular organelle crystallizing agent(s) adapted for such use, and to methods for the treatment of cancer cells by administering cellular organelle crystallizing agent(s).

BACKGROUND OF THE INVENTION

Surgery and non-surgical anti-cancer therapies such as radiotherapy, chemotherapy, photodynamic therapy, immunotherapy, electric/chemotherapy, hyperthermia therapy, hyperbaric oxygen therapy, ischemia/reperfusion therapy and gene therapy have been found to be effective in the treatment of cancer. However, all of these treatments have been limited by tumor recurrence. In recent years, fundamental advances have been made in the development of regimens for solving these problems. Cancers continue to be the most common cause of death in countries throughout the world. The need for new and effective methods for treating cancer and leukemia continues to fuel efforts to find new classes of anti-tumor compounds or methods, especially for the inoperable or metastatic solid tumors, such as the various forms of lung cancer and hepatic carcinoma.

The characteristics and functions of cells are determined and maintained by cellular organelles and cellular cytoskeleton. Cellular organelles include nucleus, mitochondria, peroxisomes, Golgi apparatus, endoplasmic reticulum, centrosome, and vacules. Cytoskeletal structures (cytoskeleton) refer to an extensive scaffolding of fibrillar elements, including the three filamentous systems: microfilaments (or actin filaments), microtubules, and intermediate filaments. It may also include linin filaments. The components of the cytoskeleton are involved in diverse cellular functions ranging from mitosis to cell motility to signal transduction. In essence, the intact structure of the cytoskeleton and organelles constitutes the foundation of cell life, especially in the development of a variety of resistances. Among these organelles and cytoskeletal structures, the centrosome, microtubules, mitochondrion, and nuclear envelope are most important.

The centrosome, a central body (or the major microtubule organizing center (MTOC) of the cell, is composed of two centrioles surrounded by the so-called pericentriolar material (PCM), which consists of a complex thin filament network and two sets of appendages (Paintrand, M. (1992) *J Struct Biol* 108: 107-128). The centrosome, a thixotropic blob, is believed to play a key role in the temporal and spatial distribution of the interphasic and mitotic microtubule network and is regarded as a major determinant of the overall organization of the cytoplasm and of the fidelity of cell division (Hsu, L. C. and White, R. L. (1998) *Proc Natl Acad Sci USA* 27; 95(22): 12983-8). Cytoplasmic organization, cell polarity and the equal partition of chromosomes into daughter cells at the time of cell division, once and only once in each cell cycle, are all ensured through the actions of tightly regulated centrosomal function (Tanaka, T., et al., (1999) *Cancer Res* 59(9): 2041-4). Centrosome association occurs throughout the mammalian cell cycle, including all stages of mitosis, and determines the number, polarity, and organization of interphase and mitotic microtubules (Tanaka, T., et al., (1999) *Cancer Res* 59(9): 2041-4; Pihan, G. A., et al., (1998) *Cancer Res* 58(17): 3974-85). The main function of the centrosome is the nucleation of microtubules and the formation of bipolar spindles (Tanaka, T., et al., (1999) *Cancer Res* 58(17): 3974-85). Centrosomes and their associated microtubules direct events during mitosis and control the organization of animal cell structures and movement during interphase. The microtubule nucleating ability of centrosomes of tissue sections retain even after several years of storage as frozen tissue blocks (Salisbury, J. L., et al., (1999) *J Histochem Cytochem* 47(10):1265-74).

Malignant tumors generally display abnormal centrosome profiles, characterized by an increase in size and number of centrosomes, by their irregular distribution, abnormal structure, aberrant protein phosphorylation, and by increased microtubule nucleating capacity in comparison to centrosomes of normal tissues (Lingle, W. L. et al., (1998) *Proc Natl Acad Sci USA* 95(6): 2950-5; Sato. N., et al., (1999) *Clin Cancer Res* 5(5):963-70; Pihan, G. A., et al., (1998) *Cancer Res* 58(17):3974-85; Carroll, P. E., et al., (1999) *Oncogene* 18(11): 1935-44; Xu, X., et al., (1999) *Mol Cell* 3(3):389-95; Brinkley, B. R., et al., (1998) *Cell Motil Cytoskeleton* 41(4): 281-8; Doxsey, S. (1998) *Nat Genet* 20(2):104-6; Kuo, K. K., et al., (2000) *Hepatology* 31(1):59-64). Among the abnormalities, centrosome hyperamplification is found to be more frequent in a variety of tumor types (Carroll, P. E., et al., (1999) *Oncogene* 18; 18(11):1935-44; Hinchcliffe, E. H., et al., (1999) *Science* 283(5403):851-4; Xu, X., et al., (1999) *Mol Cell* 3(3):389-95; Weber, R. G., et al., (1998) *Cytogenet Cell Genet* 83:266-269). Although the precise mechanisms by which the centrosomes are (up) regulated during cell cycle are largely unknown, the over-expression of centrosomal kinases or the lack of tumor suppressor genes are observed universally in malignant tumors (Carroll, P. E., et al., (1999) *Oncogene* 18; 18(11):1935-44; Mussman, J. G., et al., (2000) *Oncogene* 23; 19(13):1635-46; Zhou, H., et al., (1998) *Nat Genet* 20(2): 189-93).

Except for the known keyproteins, such as SKP1p, cyclin-dependent kinase 2-cyclin E (Cdk2-E) (Hinchcliffe, E. H., et al., (1999) *Science* 283(5403): 851-4), kendrin (Flory, M. R., et al., (2000) *Proc Natl Acad Sci USA* 23; 97(11):5919-23), protein kinase C-theta (Passalacqua, M., et al., (1999) *Biochem J* 337(Pt 1): 113-8), and EB1 protein, a variety of new cell cycle-regulated kinases or tumor suppressor genes are found to be located in or to be core components of the centrosome. They include Nek2 (Fry, A. M., et al., (1999) *J Biol Chem* 274(23): 1304-10), protein kinase A type II isozymes (Keryer, G., et al., (1999) *Exp Cell Res* 249(1):131-146), heat shock Cognate 70 (HSC70) (Bakkenist, C. J., et al., (1999) *Cancer Res* 59(17):4219-21), PH33 (Nakadai, T., et al., (1999) *J Cell Sci* 112 (Pt9): 1353-64), AIKs (Kimura, M., et al., (1999) *J Biol Chem* 274(11)7334-40), human SCF (SKP2) subunit p19(SKP1) (Gstaiger, M., et al., (1999) *Exp Cell Res* 247(2)554-62), STK15/BTAK (Zhou, H., et al., (1998) *Nat Genet* 20(2): 189-93), C-Nap1 (Fry, A. M., et al., (1998) *J Cell Biol* 274(23): 1304-10), Tau-like proteins (Cross, D., et al., (1996) *Exp Cell Res* 229(2):378-87), cyclin E (Carroll, P. E., et al., (1999; Mussman, J. G., et al., (2000) *Oncogene* 23; 19(13): 1635-46), retinoblastoma protein pRB and BRCA1 (Hsu, L. C., et al., (1998) *Proc Natl Acad Sci USA* 95(22):12983-8; Carroll, P. E., et al., (1999) *Oncogene* 18; 18(11): 1935-44). These proteins are required in the initiation of DNA replication and mitotic progression (Gstaiger, M., et al., (1999) *Exp Cell Res* 15; 247(2):554-62).

As with most biological processes and particularly with the processes of cell cycle control and signal transduction, the story is more complicated than appears at first sight. It is likely that the proteins or kinases identified to be associated with centrosome dysfunction are only the couple of many in a complex pathway (or parallel pathway) that controls centrosome assembly and function. Support for this idea comes from other new molecules that were reported lately. For example, BTAK/AIK1 (Tanaka, T., et al., (1999) *Cancer Res* 59(9): 2041-4), AIK3 (Kimura, M., et al., (1999) *J Biol Chem* 274(11):7334-40), Mdm2 (Carroll, P. E. et al., (1999) *Oncogene* 18; 18(11): 1935-44) and STK15/BTAK (Zhou, H., et al., (1998) *Nat Genet* 20: 189-193) are reported to be associated with centrosome dysfunction. The changes such as the loss of p53 tumor suppressor protein and/or the overexpression of these centrosome kinases may cause abnormal centrosome function, abnormal spindle formation, and chromosome segregation (Carroll, P. E. et al., (1999) *Oncogene* 18; 18(11):1935-44; Zhou, H., et al., (1998) *Nat Genet* 20:189-193; Tanaka, T., et al., (1999) *Cancer Res* 59: 2041-44).

It is therefore not difficult to envision how hard could it be to control the aggressive division of cancer cells by inhibiting one or some group of molecules. There are no methods or agents that have been reported to choose the centrosome as a target for this purpose.

Microtubules, a filamentous system, are linear polymers of alpha-and beta (the beta 1, beta2, and beta4 isotypes)-tubulin heterodimers. Except for being a frame of cellular membrane and organelles, microtubules are involved in diverse cellular functions ranging from mitosis to cell motility to signal transduction. Microtubules are the major constituents of mitotic spindles, which are essential for the separation of chromosomes during mitosis (Shan, B., et al., (1999) *Proc Natl Acad Sci USA* 96(10):5686-5691). They are nucleated by the centrosome through the kinetochores of the centrosome. The spindle is a microtubule-based superstructure that assembles during mitosis to separate replicated DNA. Chromosome attachment to and movement on the spindle is intimately tied to the dynamics of microtubule polymerization and depolymerization. The sister chromatid pairs must maintain a stable attachment to spindle microtubules as the microtubules interconvert between growing and shrinking states. Drugs that are currently used in cancer therapy were designed to perturb microtubule shortening (depolymerization) or lengthening (polymerization) (Compton, D. A., et al., (1999) *Science* 286: 913-914). Unfortunately, a variety of these drugs (such as paclitaxel, docetaxel, etoposide, vincristine, vinblastine, and vinorelbine) are limited by the fact that they all share a common mechanism of action: They bind to tubulin, the molecule of which microtubules are composed, and arrest cells in mitosis by inhibiting spindle assembly (Compton, D. A., et al., (1999) *Science* 286:313-314). Most recently, some agents (such as monastral) were found, in the in vitro studies, to be able to inhibit mitosis by blocking the function of essential proteins (Mayer, T. U., et al., (1999) *Science* 286: 971-974). However, proteins involved in the assembly and the maintenance of the mitotic spindle may be tremendous. For example, one class of such proteins is the family of mitotic kinesins, a subset of the kinesin superfamily (Mayer, T. U., et al., (1999) *Science* 286: 971-974). This superfamily contains over 100 proteins. In addition, as described previously, many key proteins are located in or are the components of centrosome and/or microtubules. Targeting one specific protein out of this tremendous number of proteins is hardly likely to bring a satisfying inhibition of cell mitosis. The consequent problem will inevitably be the development of a variety of resistances as seen with other drugs due to the strong regulating ability of the cancer cells.

Other cytoskeletons such as membrane skeleton, microvilli, cilia, flagella, microfilaments, actin filaments, contractile ring, and intermediate filaments are all important in the organization of the cytoplasm and of the fidelity of cell division.

Except for centrosome and microtubules, other cell organelles or cellular sub-organelles such as mitochondrion, chromosomes, chromatin, nuclei, nuclear matrix, nuclear lamina, core filaments, nuclear envelope (NEs), nuclear pore complexes (NPCs), nuclear membrane, centrioles, pericentriolar materials (PCM), mitotic spindle, spindle pole bodies (SPBs), contractile rings, proteasomes, telomere, plasma membranes, Golgi complexes, Golgi apparatus, endoplasmic reticulum (ER), lysosomes, endosomes, peroxisomes, phagosomes, ribosomes, are all important in maintaining a cell's life. The endoplasmic reticulum, e.g., is the site of synthesis and maturation of proteins.

In the past decades, almost all anti-cancer techniques have focused on the inhibition of the elevated cancer products or the oncogenes that code these products. As the powerful regulating ability and self-defense mechanisms of the aggressively growing cancer cells (Kong, Q. and Lillehei, K. O. (1998) *Med Hypotheses* 51: 405-409) are greatly ignored, a satisfying outcome following traditional therapies has never been obtained. The commonly recognized reason is likely the development of a variety of resistances prior to recurrence. Thus, there is a need for the development of novel, more effective cancer therapies.

SUMMARY OF THE INVENTION

A general object of this invention is to provide a novel method for treating cancer.

It is also a general object of this invention to provide a novel class of anticancer agents having improved therapeutic efficacy.

It is also a general object of this invention to provide a novel method for cancer therapy using cellular organelle and/or cytoskeleton crystallizing agents.

It is a further object of this invention to provide a method for selectively increasing the susceptibility of tumor cells to other non-surgical anticancer therapies.

It is a still further object of this invention to provide a method for treating cancer that has minimal side effects.

It is another object of this invention to provide a method for treating cancer that reduces or eliminates the potential for the development of tumor resistance (multi-drug resistance or cross-resistance).

It is yet another object of this invention to provide a composition for treating cancer comprising a therapeutically effective amount of a crystallizing agent.

It is also an object of this invention to provide a composition for treating cancer comprising therapeutically effective amounts of a crystallizing agent and a therapeutic agent.

Additional objects, advantages and novel features of this invention shall be set forth in part in the description that follows, and in part will become apparent to those skilled in the art upon examination of the following specification or may be learned by the practice of the invention. The objects and advantages of the invention may be realized and attained by means of the instrumentality, combinations, and methods particularly pointed out in the appended claims.

To achieve the foregoing and other objects and in accordance with the purposes of the present invention, as embodied and broadly described therein, the present invention comprises administering to a mammalian host a therapeutically effective amount of a crystallizing agent. The crystallizing agent may be any tetrazolium salt. The crystallizing agent may also be a substrate of other dehydrogenases such as succinate dehydrogenase, lactate dehydrogenase and oxidative reductases.

The present invention is also directed to a method for treating tumor cells in a mammalian host which comprises administering to the host a crystallizing agent in an amount effective for sensitizing the tumor cells to an anticancer therapy.

The present invention further includes a method for treating cancer cells in a mammalian host which comprises conjointly administering to the host an crystallizing agent and a dose of a cancer therapy, the crystallizing agent being administered in an amount sufficient to sensitize the cancer cells. The crystallizing agent may be administered concurrently with the anticancer therapy.

The present invention is also directed to a composition composing a therapeutically effective amount of a crystallizing agent, such as tetrazolium red and tetrazolium violet. The composition may comprise a pharmaceutically acceptable carrier medium, such as a biocompatible, biodegradable polymer. The biodegradable polymer may be a polylactic acid polymer or a copolymer substance comprising polylactic acid.

The present invention also includes a composition comprising a therapeutically effective amount of a crystallizing agent and a pharmaceutically effective amount of a therapeutic agent.

BRIEF DESCRIPTION OF THE DRAWINGS

The accompanying drawings, which are incorporated in and form a part of the specification, illustrate the preferred embodiments of the present invention, and together with the descriptions serve to explain the principles of the invention. The patent or applicatin file includes at least one drawing executed in color. Copies of this patent or patent application with color drawing(s) will be provided by the Office upon request and payment of the necessary fee.

DETAILED DESCRIPTION OF THE PREFERRED EMBODIMENTS

The inventor of the present invention has found that succinate dehydrogenase (SDH) and/or other enzymes such as oxidation reductases are highly expressed in cancer cells. Except in mitochondrion, it is widely expressed in other cellular structures such as, but not limited to, centrosomes, microtubules, flagella, and nuclear envelopes etc. This finding is contrary to the established view on the cellular distribution of SDH in mammalian cells. When tetrazolium salts are present with viable cells, cellular dehydrogenases such as SDH, which are usually anchored on the cellular structures, can reduce the tetrazolium salts into related crystals. The more the enzymes are expressed, the more the crystals are formed. Based on these findings, the inventor of this invention takes full advantage of the oncogene products instead of inhibiting them, which is expected to avoid the critical problem of the development of resistances in cancer therapy. The formation of crystals may result in both mechanical injuries to cellular structures that are usually very flexible and functional impairment. For example, crystallization of microtubules not only damages cell membranes but also changes the moving track of small molecules and signal transduction, or alters the spindle check-point mechanism during cell mitosis. Crystallization of centrosomes not only limits the formation of spindles and the segregation of chromosomes but also interferes with the signal transductions from and/or to centrosomes. In other words, all key enzymes located in the targeted structures of the cell cannot function normally. The formation of crystals may act as a restraint on the separation and movement of the duplicable organelles and cytoskeletons. The cellular structures that are rich in SDH and key enzymes in these structures will be functionally and structurally frozen or locked. To better distinguish from the known cell death (apoptosis and necrosis), this "cellular-organelle (and/or cytoskeleton)-crystallization-induced-death" is referred to herein as "Cocid".

The cell-mediated reduction of tetrazolium salts has long been used as a cell number-counting method (Bernas, T., et al., (1999) *Biochim Biophys Acta* 12; 1451(1):73-81; Abe, K., and Saito, H., (1999) *Brain Res* 29; 830(1):146-54; Liu, Y., et al., (1997). *J Neurochem* 69(2):581-93). In cancer therapy, the application of tetrazolium salts has never been mentioned. The inventor of this invention has found that tetrazolium salts can specifically target and concentrate on cellular organelles and/or cytoskeletons of a variety of cancer cells, with the formation of crystals in these places. The method of this invention exerts its cancer-killing effect through freezing the whole cellular organelle and/or cytoskeleton instead of inhibiting specific molecules. For example, the crystallization of a tumor cell's centrosome is like freezing or locking the "brain" of a cell. However, the simple inhibition of a certain molecule as seen with the conventional methods is like cutting off a leaf or a branch of a tree. Therefore, the potential of the present invention as an alternative in the battle of conquering cancer is great.

In summary, this invention provides a method for treating cancer through the cocid mechanism, a method for treating cancer using cellular organelle (and/or cytoskeleton) crystallizing agents (COCAs), compositions containing COCAs that are adapted for such use, and methods for the treatment of cancer cells by administering COCA(s).

The method of this invention involves administering to a mammalian host, preferably a human host, therapeutically effective amounts of one or more crystallizing agents. The crystallizing agent is a compound or composition that is a substrate of cellular enzymes. Preferably, the crystallizing agent is a tetrazolium salt such as tetrazolium blue, tetrazolium violet or tetrazolium red, and the enzyme is a dehydrogenase such as succinate dehydrogenase (SDH). The crystallizing agent such as tetrazolium blue, tetrazolium violet or tetrazolium red is catalyzed by said enzyme such as SDH with the formation of crystals. The formation of crystals may cause in the targeted cells a variety of changes, which include: but not are limited to, mechanical injury of cellular structures; deactivation of key enzymes; freezing of the targeted structures, blocking of signal transduction, cessation of cell mitosis. The methods of the invention also include a method of enhancing the effect of an anticancer therapy, which method comprises administering conjointly with the therapy an effective amount of a crystallizing agent. In another aspect, the present invention provides a composition suitable for administration to mammalian hosts comprising a therapeutically effective amount of a crystallizing agent. In yet another aspect, the invention provides a composition suitable for administration to mammalian hosts comprising a mixture, in therapeutically effective amounts, of at least one crystallizing agent and at least one pharmaceutically acceptable agent.

Unless defined otherwise, all technical and scientific terms used herein have the same meaning as commonly understood by one of ordinary skill in the art to which this invention pertains. Although any methods and materials similar or equivalent to those described herein can be used in the practice of the present invention, the preferred methods and materials are described.

As used herein, the term "crystallizing agent" refers to a substance that, when present in a living cell or medium containing enzymes that catalyze dehydrogenating reactions, can form crystals. Preferred crystallizing agents are tetrazolium salts and related derivatives or analogues. Tetrazolium salts are compounds with tetrazole, tetrazolyl, or tetrazolo-structure. The tetrazolium salt is an organic salt in which the organic portion contains one or two tetrazole rings, generally with aryl (especially phenyl or substituted phenyl) or naphthyl, substituents at various positions, particularly the 1, 2, 3, and 5 positions. Tetrazolium salts with two tetrazole rings are typically coupled so as to provide a diphenyl group or naphthyl group with the tetrazole rings in the two para positions. Exemplary tetrazolium compounds of this invention include the following: pABT (p-Anisyl Blue Tetrazolium Chloride); pApNBT, p-Anisyl-p-Nitro Blue Tetrazolium Chloride; BSPT, Thiazolyl blue (2-2'-Benzothiazolyl-5-styryl-3-(4'-phthalhydrazidyl)tetrazolium chloride); B T, Blue tetrazolium chloride; BTSPT, 2-(2'-Benzothiazolyl)-5-styryl-3-(4'-phthalhydrazidyl)-tetrazolium chloride; CTC, (5-Cyano-2,3-ditolyl tetrazolium chloride); DMDPT, [3-(4,5-Dimethylthiazol-2-yl)-2,5-diphenyl]tetrazolium Bromide, 1-[4,5-dimethylthiazol-2-yl]-2,5-diphenyltetrazolium bromide; DSNBT, Distyryl nitroblue tetrazolium chloride; (1H)-tetrazole; IDNTT, Iodonitrotetrazolium chloride; INT, Iodo Nitro Tetrazolium Violet Chloride, p-iodo nitrotetrazolium violet (2-(4-iodophenyl)-3-(4-nitrophenyl)-5-phenyltetrazolium chloride); INpT, 2-(p-iodophenyl)-p-nitrophenyl-5-phenyltetrazolium chloride; mNBT, m-Nitro Blue Tetrazolium Chloride; mNNT, m-Nitro Neotetrazolium Chloride; MNSTC, 2,2-bis(2-methoxyl-4-nitro-5-sulfophenyl)-2H-tetrazolium-5-carboxanilide; MTS: 3-(4,5-dimethylthiazol-2-yl)-5-(3-carboxymethoxyphenyl)-2-(4-sulfophenyl)-2H-tetrazolium salt; MTT, tetrazolium bromide, thiazolyl blue tetrazolium bromide, (3->4,5-dimethylthiazol-2-yl!-2,5-diphenyltetrazolium bromide); NBMT, Nitro Blue Monotetrazolium Chloride; NBT, p-Nitro Blue Tetrazolium Chloride, Nitro blue tetrazolium chloride (2,2'-di-nitrophenyl-5,5'-diphenyl-3,3'-(3,3'-dimethoxy-4,4'-diphenylene)ditetrazolium chloride); NT, Neotetrazolium chloride (2,2',5,5'-Tetraphenyl-3,3'(p-diphenylene)-ditetrazolium chloride; NTV, Nitrotetrazolium Violet; Thiazolyl blue; TB, tetrazolium blue chloride (3,3'->3,3'-dimethoxy(1,1'-biphenyl)-4,4'-diyl]-bis(2,5-diphenyl-2H-tetrazolium)dichloride); NBT, Nitroblue tetrazolium chloride; oTTR, o-Tolyl Tetrazolium Red; PCTMB, sodium 3'-[1-[(phenylamino)-carbonyl]-3,4-tetrazolium]-bis(4-methoxy-6-nitro)benzene-sulfonic acid hydrate; PNBT, p-Nitro Blue Tetrazolium Chloride; PTB, Piperonyl Tetrazolium Blue; pTTR, p-Tolyl Tetrazolium Red; TC-NBT, Thiocarbamyl nitro blue tetrazolium chloride (2,2'-di-p-nitrophenyl-5,5'-di-p-thiocarbamylphenyl-3,3'[3,3'-dimethoxy-4,4'-biphenylene]-ditetrazolium chloride; TNBT, Tetranitroblue tetrazolium chloride; TPTT, 1,3,5-triphenyltetrazolium; TR, TTC, TPT, Tetrazolium Red (2,3,5-triphenyltetrazolium chloride); TV, Tetrazolium violet, Violet Tetrazolium, 2,3,5-Triphenyl-2-H-tetrazolium chloride, 2,5-diphenyl-3-[.alpha.-naphthyl]-tetrazolium chloride, 2,5-diphenyl-3-[1-naphthyl]-2H-tetrazolium chloride; VTB, Veratryl tetrazolium blue; WST-1: 4-[3-(4-iodophenyl)-2-(4-nitrophenyl)-2H-5-tetrazolio]-1,3-benzene disulfonate; XTT, 2,2-bis(2-methoxyl-4-notro-5-sulfophenyl)-2H-tetrazolium-5-carboxanilide. Preferably, the crystallizing agent is selected from one or more member of the group consisting of tetrazolium violet, CTC, MTT, Tetrazolium Blue, HTT, tetrazolium red, TPF, ITT, INT, INPT, neotetrazolium chloride, NBT, TNBT, TC-NBT, TTD, MTS, WST-1, XTT, DDTT, and PCTT. Most preferably, the crystallizing agent is selected from one or more member of the group consisting of tetrazolium violet, CTC, MTT, Tetrazolium Blue, and tetrazolium red.

As used herein, the term "enzyme" refers to a substance that, when present in a living cell or medium containing their substrates, catalyzes dehydrogenating reactions. Enzymes can function in several ways: by dehydrogenating substances such as succinic acid or succinate (hereinafter referred to as "substrate") to provide cellular energy, or by catalytically converting salts such as tetrazolium salts to related formzan crystals. The enzymes that may catalyze the formation of crystals are, but not are limited to, oxidation reductases, DT-diaphorase, alcohol dehydrogenase, beta-hydroxysteroid dehydrogenase, inosine monophosphate dehydrogenase, glucose .alpha.-dehydrogenase, glucose-6-phosphate dehydrogenase, glyceraldehyde-3-phosphate dehydrogenase, glycerol-3 phosphate dehydrogenase (mGPDH), malate dehydrogenase, 3-.alpha.-hydroxysteroid dehydrogenase, lactate dehydrogenase, L-glutamate dehydrogenase, leucine dehydrogenase, aldehyde dehydrogenase, sarcosine dehydrogenase, amine dehydrogenase, succinate dehydrogenase, choline dehydrogenase, fructose dehydrogenase and sorbitol dehydrogenase. Preferably, such enzymes are inosine monophosphate dehydrogenase, telomerase, glucose-6-phosphate dehydrogenase, malate dehydrogenase, lactate dehydrogenase, and succinate dehydrogenase. Preferably, the enzyme is a dehydrogenase such as, but not limited to, SDH, inosine monophosphate dehydrogenase, glucose-6-phosphate dehydrogenase, malate dehydrogenase, and lactate dehydrogenase. More preferably, the enzyme is SDH, and lactate dehydrogenase.

As used herein, the term "cytoskeleton" refers to a complex network of protein filaments traversing the cell cytoplasm. It is not simply a passive feature of the cell that provides structural integrity, it is a dynamic structure that is responsible for whole-cell movement, changes in cell shape, and contraction; it provides the machinery to move organelles from one place to another in the cytoplasm. Some cytoskeletal fibers may connect to organelles or provide tracks along which organelles and/or small molecules move. It is recently evidenced that the cytoskeleton is a master organizer of the cell's cytoplasm, furnishing binding sites for the specific localization of ribonucleic acids (RNAs) and proteins that were once thought to diffuse freely through the cytoplasm. The cytoskeleton is also responsible for signal transduction. Activities of the cytoskeleton depend mainly on just three principal types of protein assemblies: actin filaments, microtubules, and intermediate filaments. Each type of filament or microtubule is formed from specific association of protein monomers. The dynamic aspects of the cytoskeletal structures arise from accessory proteins that control the length of the assemblies, their position within the cell, and the specific-binding sites along the filaments and microtubules for association with protein complexes, organelles, and the cell membrane. Thus, the present invention also includes the crystallization of these proteins, protein monomers, and protein filaments. Dynamically, crystallization of microtubules, centrosomes, and other cytoskeletons may interfere with the message (or signal) transmission or cell motility, and consequently make the cells lacking in mitosis motive force. The crystallization of nuclear envelopes may block the duplication of chromatins, and therefore obstruct the formation of daughter cells.

As used herein, the term "organelle" refers to a subcellular unit or a subcellular structure defined by plasma membrane. The organelle in this invention includes, but is not limited to, nucleus (containing most of the cellular DNA and being the site of synthesis of cellular RNAs), nuclear matrix, nuclear lamina, core filaments, nuclear envelope (NEs), nuclearpore complexes (NPCs), and nuclear membranes. The organelle in this invention also includes mitochondrion, endoplasmic reticula (ER, a network of membranes in which glycoproteins and lipid are synthesized), Golgi complexes or Golgi apparatus (directing membrane constituents to appropriate places), lysosomes (degrading proteins, nucleic acids and lipids), and vacuoles (large fluid-filled organelles that store many nutrient and waste molecules, and also participate in the degradation of cellular proteins and other micromolecules). The organelle in this invention further includes chromosomes, nucleosome, chromatin, centromere, centrosome, centrioles, pericentriolar material (PCM), mitotic spindle, spindle pole bodies (SPBs), contractile rings, kinetochore, proteasomes, telomere, plasma membranes, endosomes, peroxisomes (metabolizing hydrogen peroxide), phagosomes, and ribosomes. Each type of organelle plays a unique role in the growth, metabolism, and metastasis of tumor cells, and each contains a collection of specific proteins or enzymes that catalyze the requisite chemical reactions. Some of this specificity resides in the organelle membranes, to which a number of the enzymes and other proteins are bound. In this invention, dehydrogenases, particularly succinate dehydrogenase (SDH), are found to be highly expressed in such organelles of a variety of cancer cells. Through the SDH-catalyzed dehydrogenating reaction, some chemicals such as tetrazolium salts can be reduced to the related formazan crystals. The crystallization of the organelles and/or cytoskeleton that are rich in SDH will have their functions and structures destroyed (frozen). The proteins or enzymes located in the structures that are rich in SDH will be inactivated or frozen.

As used herein, the term "chemotherapeutic agent" refers to a chemical compound or composition capable of inducing cell death in a cell culture or a mammalian host tissue when properly administered to the host tissue. Chemotherapeutic agents that may be utilized in the present invention include any known chemotherapeutic agent or drug, or any combination of chemotherapeutic agents or drugs, which achieve a cytotoxic effect at least in part through interfering with cellular structure and/or metabolism. Suitable chemotherapeutic agents may be derived from any source, and include synthetic, semi-synthetic, naturally occurring, and recombinant compounds. Examples of conventional chemotherapeutic agents that are particularly effective in the methods of te present invention include, without limitation, acalacinomycin, alitretinoin, allopurinol, altretamine, anastrozole, arsenic trioxide, asparaginase, busulfan, calusterone, camptothecin, capecitabine, carmofur, cladribine, dacarbazine, dexrazoxane, docetaxel, doxifloridine, doxorubicin, dromostanolone, epirubicin, estramustine, etoposide, exemestane, floxuridine, fludarabine, fluorouracil, fulvestrant, gemcitabine, homoharringtonine, hydroxycamptothecin, hydroxyurea, irinotecan, letrozole, levamisole, mesna, mitotane, mitoxantrone, oxaliplatin, paclitaxel, pipobroman, pirarubicin, Sarmustine, semustine, tamoxifen, tegafur-uracil, temozotomide, teniposide, testolactone, thioguanine, thiotepa, topotecan, valrubicin, vinblastine, vincristine, vindesine, and vinorelbine. Preferably, one antimetabolite and one alkylating agent are combined which have different tumor killing mechanisms are combined. As new chemotherapeutic agents and drugs are identified and become available to the art, they may be directly applied to the practice of the present invention.

As used herein, the term "pharmaceutically acceptable" refers to a carrier medium, which does not interfere with the effectiveness of the biological activity of the active ingredient(s) and is not toxic to the host to which it is administered.

As used herein, the term "therapeutically effective amount" as applied to the crystallizing agent or chemotherapeutic agent refers to the amount of the component in the composition or administered to the host that results in an increase in the therapeutic index of the host. The "therapeutic index" can be defined for purposes herein in terms of efficacy (extent of tumor reduction). Suitable concentrations of the crystallizing agent can be determined by various methods, including generating an empirical dose-response curve, predicting potency and efficacy using QSAR methods or molecular modeling, and other methods used in the pharmaceutical sciences. Similarly, suitable concentrations of the chemotherapeutic agent can be determined using conventional methods.

As used herein, the term "anticancer therapy" refers to an anticancer treatment or combination of treatments that depends, at least in part, on interfering cellular structures and/or metabolism. Anticancer therapies that may be utilized in the present invention include any known anticancer methods that achieve their anticancer effects at least in part through interfering cellular structures and/or metabolism. Suitable anticancer therapies of the present invention include, without limitation, radiation therapy, immunotherapy, chemotherapy, hormone therapy, hyperthermia therapy, photodynamic therapy, electrotherapy, gene therapy, antisense therapy, hyperbaric oxygen treatment, ischemia/reperfusion therapy, and the like. As new anticancer therapies are identified and become available to the art, they may be directly applied to the practice of the present invention.

As used herein, the term "effective dose" or "therapeutically effective dose" as applied to the anticancer therapy refers to the amount or unit dose of the anticancer therapy that results in an increase in the therapeutic index of the host. Suitable doses of the anticancer therapy can be determined using well-known methods, a variety of which is known and readily available in the pharmaceutical sciences.

As used herein, "conjointly" and "concurrently" mean at a time and in an amount such that the desired sensitizing effect of the crystallizing agent is in existence or comes into existence when the primary treatment effect of the anticancer therapy is taking place.

As used herein, the term "cancer or tumor" refers to any neoplastic disorder, including carcinomas, sarcomas and carcino-sarcomas. Specific types of cancers include, without limitation, glioma, gliosarcoma, anaplastic astrocytoma, medulloblastoma, lung cancer, small cell lung carcinoma, cervical carcinoma, colon cancer, rectal cancer, chordoma, throat cancer, Kaposi's sarcoma, lymphangiosarcoma, lymphangioendotheliosarcoma, colorectal cancer, endometrium cancer, ovarian cancer, breast cancer, pancreatic cancer, prostate cancer, renal cell carcinoma, hepatic carcinoma, bile duct carcinoma, choriocarcinoma, seminoma, testicular tumor, Wilms' tumor, Ewing's tumor, bladder carcinoma, angiosarcoma, endotheliosarcoma, adenocarcinoma, sweat gland carcinoma, sebaceous gland sarcoma, papillary sarcoma, papillary adenosarcoma, cystadenosarcoma, bronchogenic carcinoma, medullar carcinoma, mastocytoma, mesotheliorma, synovioma, melanoma, leiomyosarcoma, rhabdomyosarcoma, neuroblastoma, retinoblastoma, oligodentroglioma, acoustic neuroma, hemangioblastoma, meningioma, pinealoma, ependymoma, craniopharyngioma, epithelial carcinoma, embryonic carcinoma, squamous cell carcinoma, base cell carcinoma, fibrosarcoma, myxoma, myxosarcoma, liposarcoma, chondrosarcoma, osteogenic sarcoma, leukemia, and the metastatic lesions secondary to these primary tumors. In general, any neoplastic lesion, including granuloma, may be treated according the present invention. Therefore, the term "cancer" in this invention also includes the cancer supporting components such as tumor angiogenesis, and tumor endothelial cells.

A basis of the present invention is the unexpected finding that substances such as tetrazolium salts exhibit potent anticancer activity both in vitro and in vivo. While the mechanism of action is not fully understood, and not wishing to be bound by any particular theory, it is believed that these agents exert their anticancer effect through formation of crystals on the key cellular structures including organelles and/or cytoskeleton. The formation of crystals can reduce the ability of tumor cell to provide energy (mitochondrial crystallization for example) and cease the mitosis of the targeted cells (crystallization of centrosomes, microtubules, and nuclear envelope, for example) as well. The crystallization of the centrosome will deactivate many key enzymes located on it. The crystallization of microtubules not only ceases mitosis but also causes mechanical injury of the targeted cells. The crystallization of centrosomes, microtubules and nuclear envelopes further interfere with the mobility of the cell and the transmission of cellular messages. Due to the decrease of the intracellular concentration of endogenous enzymes such as succinate dehydrogenases in the treated tumor and the freezing of the cellular cytoskeletons, cancer cells become highly susceptible to the damage induced by other treatments, particularly agents that interfere with cellular structures and metabolism. Contrasting to the changes seen in the cells induced by some typical apoptosis or necrosis inducing agents, the cellular organelle crystallization-induced cell death is found to be associated with the mechanism(s), which is different from either apoptosis or necrosis and herein referred to as "cocid".

In one aspect of the invention a crystallizing agent or a combination of crystallizing agents are used in a therapeutic composition to treat tumor cells. While it is possible to administer the crystallizing agent(s) alone, it is believed preferable to present it as part of a pharmaceutical formulation. Such pharmaceutical formulations are preferably for local use, and most preferably for intralesional administration. In accordance with this aspect of the invention, the pharmaceutical compositions comprise at least one crystallizing agent in a therapeutically effective dose together with one or more pharmaceutically acceptable carriers and optionally other therapeutic ingredients. Preferred carriers include inert, non-toxic solids (e.g., dextrose, cellulose, starch), semi-solids (e.g., glycerol sterate, polyethylene glycol, stearic acid, and propylene glycol) and liquids (e.g., buffered saline, water, ethanol). The preferred form depends on the intended mode of administration. For example, injectables can be prepared as liquid solutions or suspensions, solid forms suitable for solution or suspension in liquid prior to injection, or as emulsions. A wide variety of pharmaceutically acceptable carriers are known to those of skill in the art. If desired, the pharmaceutical composition may also contain minor amounts of non-toxic auxiliary substances such as wetting or emulsifying agents, pH buffering agents, and the like. Compositions comprising such carriers and adjuvants may be formulated, and the resulting formulations may be sterilized, using well-known conventional methods and techniques. Methods for administration are also well known in the art In one embodiment of the invention, one or more crystallizing agents are loaded in a biocompatible polymer matrix body such that a slow or sustained, preferably constant, release of the crystallizing agent(s) is achieved. The polymer matrix substrate may be formed of any of a number of biostable or biodegradable polymers that act as the carrier matrix for the crystallizing agent(s). Preferably, the biocompatible polymer matrix body is comprised of a biodegradable, resorbable polymeric material. A wide variety of suitable biodegradable polymers are known and readily available to the art including, for example, polylactic acid, poly (lactideglycolide) copolymers, polyanhydrides, cyclodextrans, polyorthoesters, n-vinyl alcohol, and other biosorbable polymers. In the examples herein, the biodegradable polymer is a polylactic acid (PLA) polymer having a molecular weight of 20,000 or 100,000. Methods of preparing impregnated biocompatible polymers are known in the art and are not parts of this invention. The impregnated biocompatible polymer can be surgically implanted into the tumor (i.e., intralesional administration) using well-known techniques. The intralesional administration of chemotherapeutic drugs using impregnated biodegradable polymers is described in (Kong, Q., et al., (1997) *J Surg Oncol* 64:268-273; Kong, Q., et al., (1998) *J Surg Oncol* 69:76-82), which are incorporated by reference herein.

According to a method of this invention, a therapeutically effective amount of a crystallizing agent is administered to a mammalian host, preferably a human host, to treat cancer. The required dosage will depend upon the nature of the cancer, the severity and course of the cancer, previous therapy, the patient's health status, the particular crystallizing agent or combination of agents, and the judgment of the treating physician. In general, a suitable effective dose of the crystallizing agent will be in the range between about 0.001 to about 1,000 milligram (mg) per kilogram (kg) of body weight of recipient per treatment, preferably in the range between about 1.0 to about 100 mg per kg of body weight per treatment. The dose is preferably administered intralesionally using a pharmaceutically acceptable carrier appropriate for the mode of administration, such as by implanting an impregnated polymeric matrix or by administering the dose in a buffered saline solution through a catheter continuously or at appropriate intervals throughout the day. When the tumor has been eradicated or reduced to an acceptable size, a maintenance dose can be administered, if necessary. Subsequently, the dosage and/or the frequency of administration can be reduced, or treatment can cease. Patients can, however, require intermittent treatment on a long-term basis upon any recurrence of the cancer.

A further basis of the present invention is the discovery that the therapeutic index of an anticancer therapy can be enhanced in in vitro and in vivo systems by concomitantly or separately treating the host with a crystallizing agent. Specifically, the present inventors have determined that crystallizing agents increase the sensitivity of tumor cells to a wide variety of anticancer therapies, namely those that depend, at least in part, on interfering with cellular structures and/or metabolism for their anticancer activity. Unexpectedly, crystallizing agents were found to potentiate the damage the tumors suffered when exposed to non-surgical anticancer treatments. Non-surgical anticancer procedures include radiation therapy, hyperthermia therapy, photodynamic therapy, electrotherapy, gene therapy, antisense therapy, and ischemia/reperfusion therapy. The present inventor's findings also suggest that crystallizing agents may be useful for enhancing or potentiating tumor damage caused by chemotherapeutic agents and drugs, immunotherapy, gene therapy, and hormone therapy. While the mechanism of the potentiation is not fully understood, and not wishing to be bound by any particular theory, it is believed that the crystallizing agents may exerts its anticancer effect by reducing the ability of the tumor cell to provide energy, damaging cellular structures and/or interfering with mitosis. Because the intracellular and/or interstitial concentrations of endogenous enzymes such as succinate dehydrogenase in the treated tumor are effectively reduced or exhausted, the tumor cells become highly susceptible to the damages induced by the primary treatments. Moreover, it is believed that the use of crystallizing agents in accordance with the methods of the invention will also minimize or eliminate the chemotherapy-induced tumor resistance (commonly referred to as "multidrug resistance") which are typically associated with conventional anticancer therapies.

Accordingly, the present invention provides a method for treating tumor cells comprising administering a crystallizing agent in an amount effective for sensitizing the cells to other anticancer therapy. The administration of a crystallizing agent increases the sensitivity of tumor cells to a wide variety of non-surgical cancer therapies, such as those listed above. Crystallizing agents may be used for the treatment of various forms of malignant diseases, particularly melanomas, adenomas, sarcomas, leukemia, hypoxic tumors, carcinomas of solid tissues, and osteogenic sarcomas. Crystallizing agents may also be used for the treatment of other neoplastic growth such as angiomas and granulomas. Treatment with crystallizing agents may also allow for more effective anticancer therapies of tumors that currently respond poorly to conventional treatments, including tumors, which have developed a resistance to such therapies. When the crystallizing agent is used to potentiate or enhance the damage to tumor cells by conventional anticancer therapies, the crystallizing agent or the combination of crystallizing agents is generally administered prior to or simultaneously with administration of the anticancer therapy, i.e., "conjointly" with the primary therapy. Specifically, when used with gene therapy, the enzymes such as SDH are preferably up regulated prior to the administration of the said crystallizing agents. The methods for up regulation of the enzymes are known in the art to the skilled person.

As will be appreciated by those skilled in this art, the required dose or "effective dose" of the anticancer therapy to be utilized in treating tumors in accordance with the methods of the invention will depend on a variety of factors. Such factors include the nature of the anticancer therapy, the nature of the cancer, the severity and course of the cancer, previous therapy, the patient's health status, the particular crystallizing agents or combination of agents, and the judgment of the treating physician. In general, the dosages of the particular therapy to be used in the present invention are fixed by the particular requirements of each situation. However, the presence of the crystallizing agent increases the number of tumor cells that are killed by the anticancer therapy. Thus, the standard, pre-set dosage of the anticancer therapy is expected to become more effective in the presence of the crystallizing agents than in their absence.

According to a method of this invention, a therapeutically effective amount of a crystallizing agent is administered to a mammalian host, preferably a human host, to selectively sensitize the tumor cells during cancer therapy. The method comprises administering to a host having cancer a crystallizing agent in an amount effective for selectively sensitizing the cancer cells to the injury. The present invention also provides a method for selectively killing cancer cells in a mammalian host, preferably a human host. The method for selectively killing cancer cells comprises conjointly administering to the host a crystallizing agent and a dose of an anticancer therapy sufficient to selectively kill the cancer cells without killing substantial numbers of normal cells. Preferably, the crystallizing agent is a substrate of the enzymes. In a particularly preferred embodiment, the substrate of the enzymes is the substrate of succinate dehydrogenase. Examples of the substrate of succinate dehydrogenase are tetrazolium salts and their analogues or derivatives. Tetrazolium salts are compounds with tetrazole, tetrazolyl, or tetrazolo-structure. Examples of tetrazolium salts include, but are not limited to, MTT, CTC, TB, Tetrazolium Blue, HTT, tetrazolium red, TPF, ITT, INT, tetrazolium violet, INPT, neotetrazolium chloride, NBT, diformazan of NBT, TNBT, TC-NBT, TTD, MTS, WST-1, XTT, DDTT, and PCTT. The required dosage of the crystallizing agent will depend upon the nature of the anticancer therapy, the nature of the cancer, the severity and course of the cancer, previous therapy, the patient's health status, the particular crystallizing agent or combination of agents, and the judgment of the treating physician. In general, a suitable effective dose of the crystallizing agent will be in the range between about 0.001 to about 1,000 milligram (mg) per kilogram (kg) of body weight of recipient per treatment, preferably in the range between about 1.0 to about 100 mg per kg of body weight per treatment. When the tumor has been eradicated or reduced to an acceptable size, a maintenance dose of the crystallizing agent and/or cancer therapy can be administered, if necessary. Subsequently, the dosage and/or the frequency of administration can be reduced, or treatment can cease.

In another aspect of the invention, at least one crystallizing agent is combined with at least one chemotherapeutic agent in a therapeutic composition to treat tumor cells. In accordance with this aspect of the invention, the pharmaceutical compositions comprise one or more crystallizing agents and one or more chemotherapeutic agent agents, each of the components being present in a therapeutically effective amount, together with one or more pharmaceutically acceptable carriers and optionally other therapeutic ingredients. Preferred carriers include inert, non-toxic solids (e.g., dextrose, cellulose, starch), semi-solids (e.g., glycerol sterate, polyethylene glycol, stearic acid, and propylene glycol) and liquids (e.g., buffered saline, water, ethanol). Compositions comprising suitable carriers and adjuvants can be formulated, prepared, and administered using conventional, well-known methods. Preferably, the crystallizing agent(s) and chemotherapeutic agent(s) are loaded in a biocompatible polymer matrix body such that a slow or sustained, preferably constant, release of the crystallizing agent(s) is achieved. The polymer matrix substrate may be formed of any of a number of biostable or biodegradable polymers that act as the carrier matrix for the crystallizing agent(s), also as discussed above. Preferably, the biocompatible polymer matrix body is comprised of a biodegradable, resorbable polymeric material, a wide variety of which are known and readily available to the art. The impregnated biocompatible polymer can be surgically implanted into a tumor using well-known techniques.

Chemotherapeutic agents suitable for use in the compositions and methods of the present invention may be any known pharmaceutically acceptable agent that depends, at least in part, on interfering with cellular structure and/or metabolism for its anticancer activity. Examples of conventional chemotherapeutic agents include, but not limited to, acalacinomycin, alitretinoin, allopurinol, altretamine, anastrozole, arsenic trioxide, asparaginase, busulfan, calusterone, camptothecin, capecitabine, carmofur, cladribine, dacarbazine, dexrazoxane, docetaxel, doxifloridine, doxorubicin, dromostanolone, epirubicin, estramustine, etoposide, exemestane, floxuridine, fludarabine, fluorouracil, fulvestrant, gemcitabine, homoharringtonine, hydroxycamptothecin, hydroxyurea, irinotecan, letrozole, levamisole, mesna, mitotane, mitoxantrone, oxaliplatin, paclitaxel, pipobroman, pirarubicin, Sarmustine, semustine, tamoxifen, tegafur-uracil, temozotomide, teniposide, testolactone, thioguanine, thiotepa, topotecan, valrubicin, vinblastine, vincristine, vindesine, and vinorelbine. These chemotherapeutic agents may be used either alone or in combination. Preferably, one antimetabolite and one antimicrotubule agent are combined. The combination containing arsenic compounds, colchicin, colchicine, colchiceine, colchisal, colchium salts, vinblastine, paclitaxel and related compounds that interfere with the cytoskeletons are most preferred. As new chemotherapeutic agents and drugs are identified and become available to the art, they may be directly applied to the practice of the present invention.

In addition, crystallizing agent(s) with or without chemotherapeutic agents can be combined with the known non-surgical anticancer techniques such as radiation, photodynamic therapy, gene therapy, antisense therapy, immunotherapy, hyperthermia, and electric therapy.

It was also found that crystallizing agent(s) and/or chemotherapeutic agents might stimulate tumor growth at low dosages. In addition to stimulating tumor growth, low dose therapies also tend to induce resistance to subsequent treatments (Kong, Q., et al., (2000) *Med Hypotheses* 55(1) 29-35). Thus, a significant advantage of the present invention is the ability to effectively deliver high dosages of crystallizing agent (s) with or without chemotherapeutic agents through the local, preferably intralesional, administration of crystallizing agent(s) with or without chemotherapeutic agents. In a particularly preferred embodiment of the invention, a biocompatible polymeric matrix device is used to provide a slow, sustained release of the active ingredient(s). Such devices not only deliver a high drug concentration to the tumor for an extended period of time (thereby enhancing the cytotoxic effect), but also minimize crystallizing agent(s)-related side effects (i.e., systemic toxicity).

The invention is further described by the following examples, which are illustrative of specific modes of practicing the invention and are not intended as limiting the scope of the invention as defined by the appended claims.

In the Examples, which follow, the biodegradable polymer was prepared in the following manner. Pre-weighed active agents and lactic acid were dissolved in dichloromethane. The resulting solution was then degassed using a vacuum pump for 5 to 24 hours. The nearly dry polymer was harvested for shaping, then further dried in an incubator at 10 to 37° C. for approximately 20 to 40 hours. The dried polymer was sterilized using gamma-irradiation and stored in a dry, cool location until use.

The terms and abbreviations used in the instant examples have their normal meanings unless otherwise designated. For example "degree C" refers to degrees Celsius; "µl" refers to microliter or microliters; "µg" refers to microgram or micrograms; "mg" refers to milligram or milligrams; "ml" means milliliter or milliliters. Unless specified otherwise, commercially available chemicals were used without purification. All scientific and technical terms have the meanings as understood by one with ordinary skill in the art. The specific examples which follow illustrate the in vivo and in vitro efficacy of certain representative compositions and are not to be construed as limiting the invention in sphere or scope. The procedures and materials may be adapted to variation in order to produce compositions and methods embraced by this invention but not specifically disclosed. Further variations of the methods to produce the same compositions in somewhat different fashion will be evident to one skilled in the art.

The present invention is more specifically illustrated by the following Examples. However, it should be understood that the present invention is not limited to such Examples, but various changes and modifications can be made without departing from the scope and spirit of the invention.

EXAMPLES

Example 1

Effect of Crystallizing Agent on 91 Gliosarcoma Tumor Cells

Figure 1A:
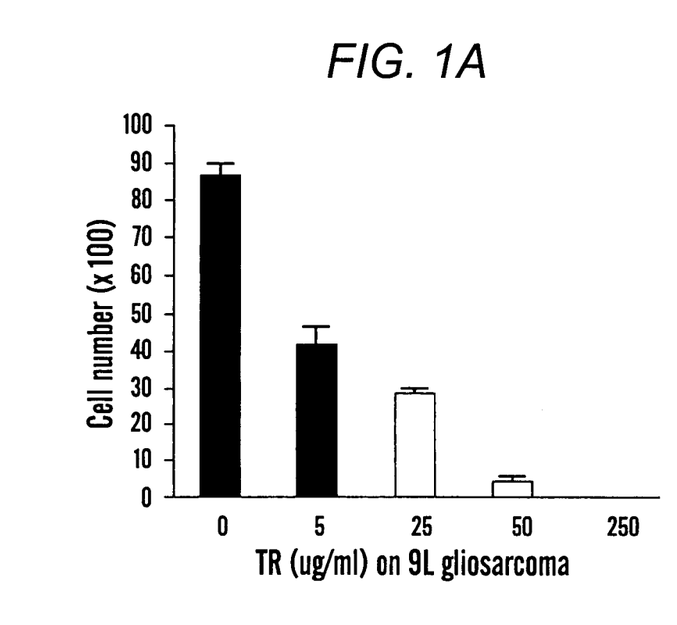
FIGS. 1A and 1B show the dose-dependent cell killing effect of tetrazolium red (TR) (FIG. 1A) and tetrazolium violet (TV) (FIG. 1B) on 9 L gliosarcoma tumor cells. The concentration of TR and TV was same ((g/ml), as indicated in the figures: 0, 5, 25, 50, and 250.
Figure 1B:
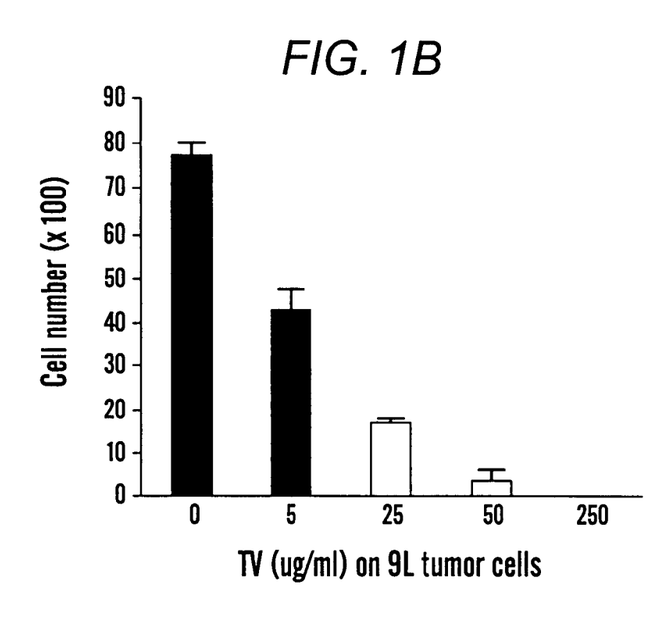

Tumor cells were exposed to escalating concentrations of SDH substrates, tetrazolium red (TR) and tetrazolium violet (TV), respectively. The tumor cells (4000) were seeded in a 48 well plate one day before treatment was administered. The concentrations of TR and TV were the same, as indicated in FIGS. 1A and 1B, respectively. The concentration was 250, 50, 25, 5, and 0 µg/ml. Tumor cell number was calculated one day post treatment. Surviving tumor cell numbers are shown in FIGS. 1A (treated with TR) and 1B (treated with TV), respectively. These data demonstrate that tetrazolium salts, the substrates of SDH are effective, in a dose dependent manner, in killing tumor cells.

Example 2

Figure 2:
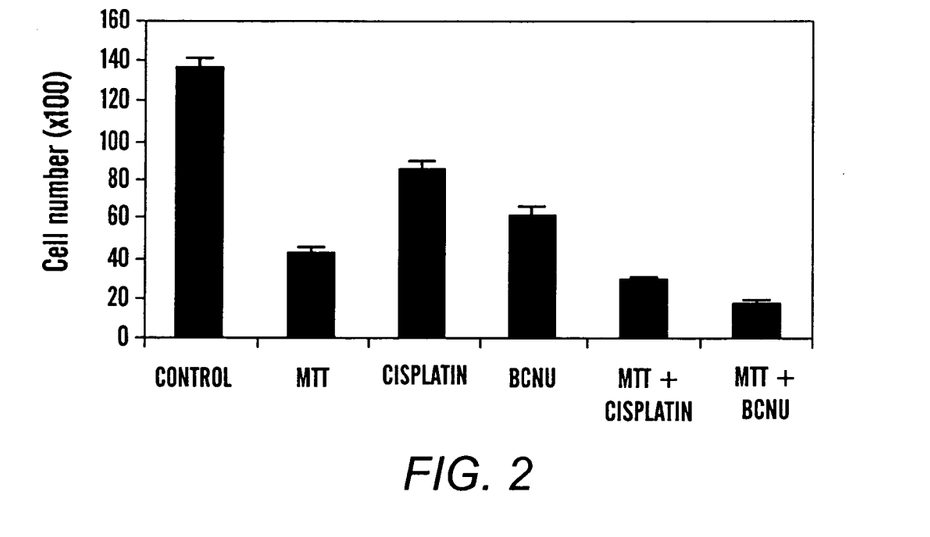
FIG. 2 shows the synergistic effect of a crystallizing agent and chemotherapeutic agent on 9 L gliosarcoma.

Synergistic Effect of Crystallizing Agent and Chemotherapeutic Agents on 91 Gliosarcoma Crystallizing agents and various chemotherapeutic agents were tested, individually and in combination, on 9 L gliosarcoma tumor cells. Treatment was administered one day after the cells (4000) were seeded in a 48 well plate, with the number of cells counted in 6 hours. MTT at 10 µg/ml was tested with cisplatin and BCNU. MTT at this dose significantly (p<0.005) enhanced the cytotoxic effects of cisplatin (10 µg/ml), and BCNU (25 µg/ml) (FIG. 2). All data represent the mean of 3 to 4 repetitions.

As is evident from FIG. 2, the crystallizing agent and chemotherapeutic agents are effective in inhibiting tumor cell growth when applied individually. However, the combination of a crystallizing agent and chemotherapeutic agents is demonstrated to be synergistic.

Example 3

In Vivo Antitumor Activity of Crystallizing Agent

Figure 3:
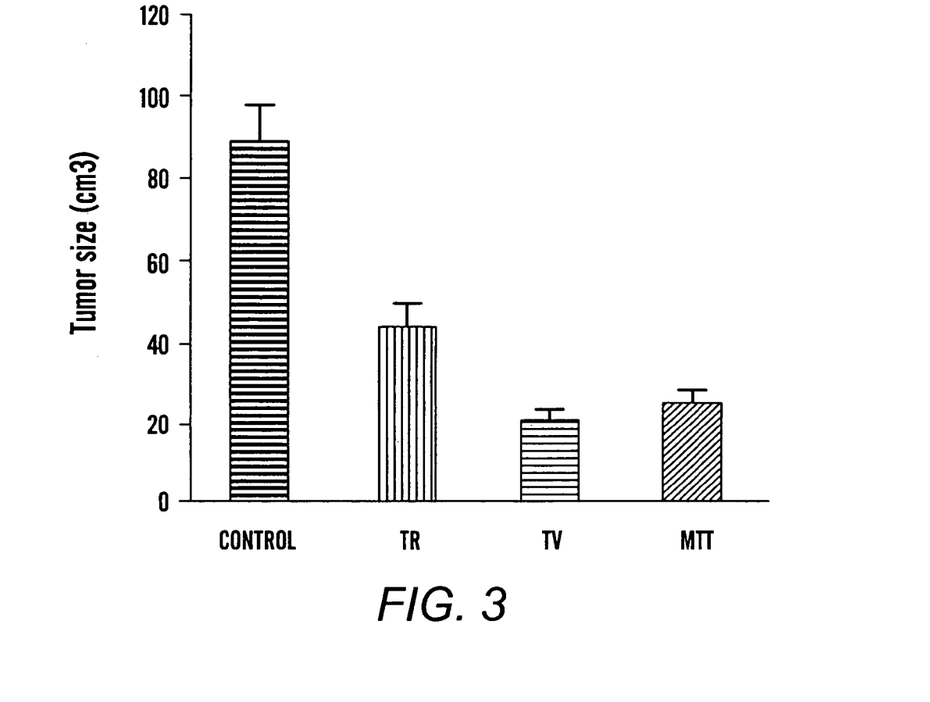
FIG. 3 shows the reduction in tumor size of established 9 L gliosarcoma in rats following treatment with tetrazolium salts impregnated into biodegradable polymer.

Small cell lung Cancer (SCLC) cells ($2\times10^5$) were injected subcutaneously in rats to test the in vivo cytotoxicity and efficacy of tetrazolium salts. Tetrazolium salts in polylactic acid polymer were implanted in rats with 14 day established 9 L gliosarcoma in the right flank area. Treatment was initiated as follows: G-1, tumor control; G-2, TR in polymer at 2.5 mg/kg; G-3, TV in polymer at 2.5 mg/kg; and G-4, MTT 2.5 mg/kg. The tumor volume was measured on day 60. The tumor size was significantly smaller ($p<0.05$) in the treated groups, as compared to tumor control (88.5 (7.8 $cm^3$). See Table 1 and FIG. 3.

TABLE 1

| Group (n) | Treatment | Tumor size ($cm^3$) | P values |
| --- | --- | --- | --- |
| 1 (6) | — | 88.5 ± 23 $cm^3$ | |
| 2 (6) | TR, 2.5 mg/kg | 44 ± 5.3 $cm^3$ | <0.05 |
| 3 (6) | TV, 2.5 mg/kg | 21 ± 2.3 $cm^3$ | <0.01 |
| 4 (6) | MTT, 2.5 mg/kg | 24 ± 3.6 $cm^3$ | <0.01 |

Example 4

Figure 4:
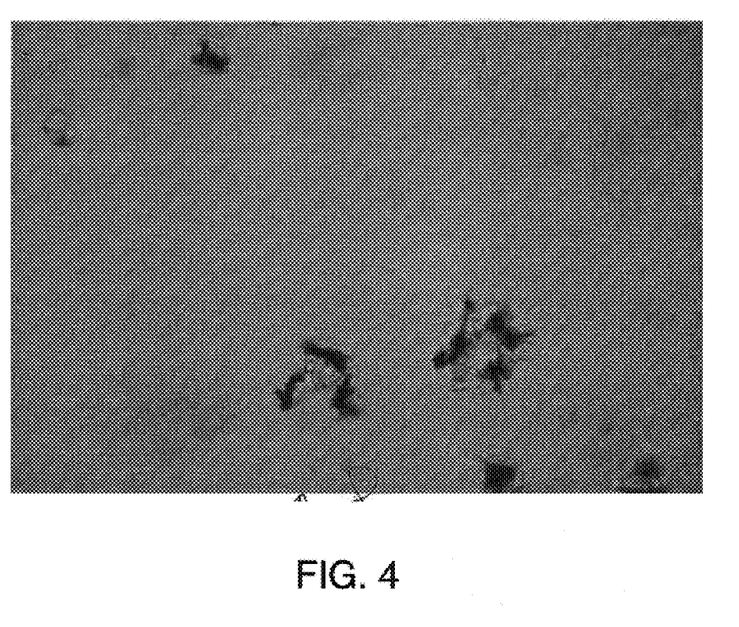
FIG. 4 shows the crystallization of centrosomes of SHP77 (SCLC) cells following treatment with tetrazolium violet (TV).

Crystallization of Centrosomes of SHP77 (Sclc) Cells Following Treatment with TV SHP77, small cell lung cancer cells (SCLC), were exposed to tetrazolium violet (TV, a substrate of SDH). The tumor cells (4000) were seeded in a 48 well plate one day before being treated. The concentration of TV was 50 µg/ml. As shown in FIG. 4, centrosomes, usually one in each cell were crystallized at the poles, with the cell viability being significantly reduced (see data in example 1).

After being treated under the same conditions, the centrosomes of 9 L gliosarcoma tumor cells were all crystallized (figures not shown).

Example 5

Figure 5:
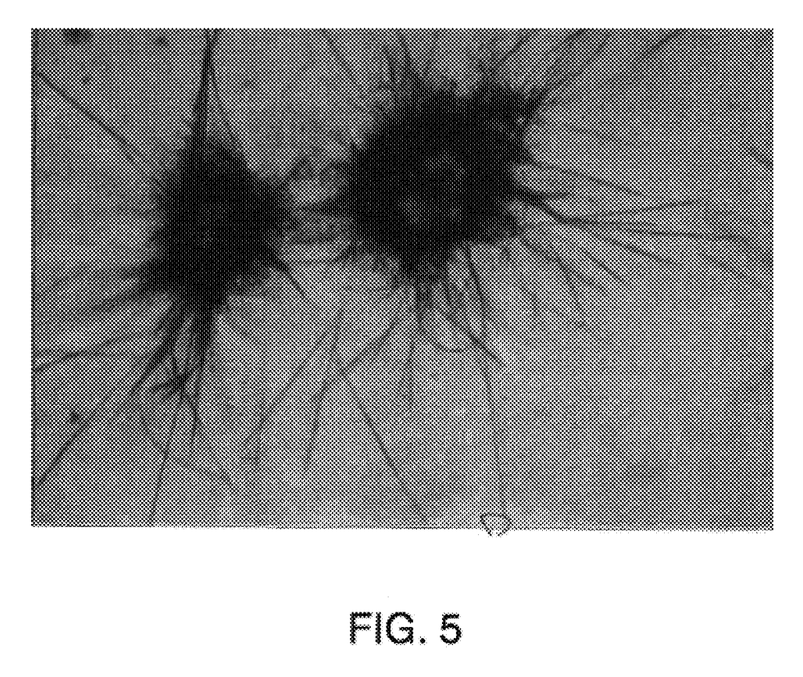
FIG. 5 shows the crystallization of microtubules of 9 L gliosarcoma cancer cells following treatment with MTT.

Crystallization of Microtubules of 9 L Gliosarcoma Cancer Cells Following Treatment with MTT 9 L cancer cells were exposed to MTT (50 µg/ml). The tumor cells (4000) were seeded one day before being treated with MTT. As can be seen in FIG. 5, crystals formed on them froze the microtubules.

Example 6

Figure 6:
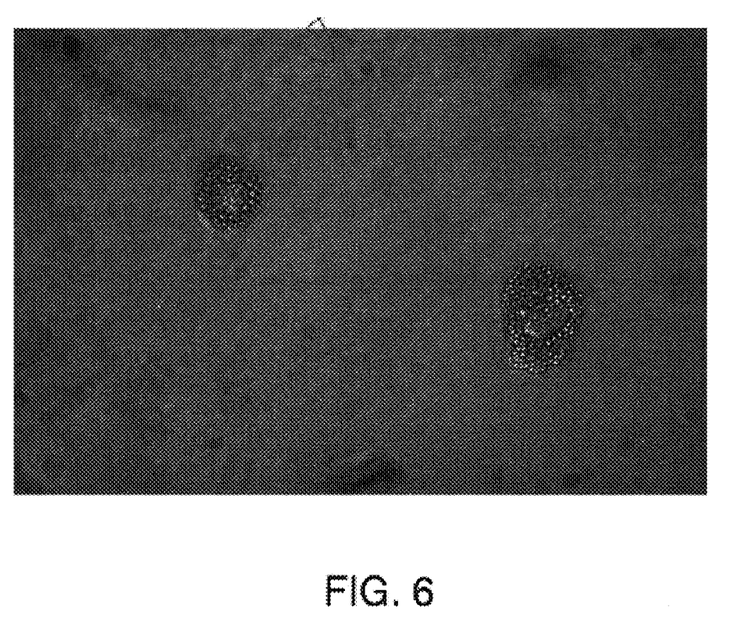
FIG. 6 shows the crystallization of mitochondrion (or lysosomes) of 9 L gliosarcoma cells following treatment with MTT.

Crystallization of Mitochondrion or Lysosomes of 91 Gliosarcoma Cells Following Treatment with MTT 9 L gliosarcoma cancer cells were exposed to MTT (50 µg/ml)—a substrate of SDH. The tumor cells (4000) were seeded one day before being treated with MTT. As can be seen, in FIG. 6, the mitochondrion or lysosomes were crystallized.

Example 7

Figure 7:
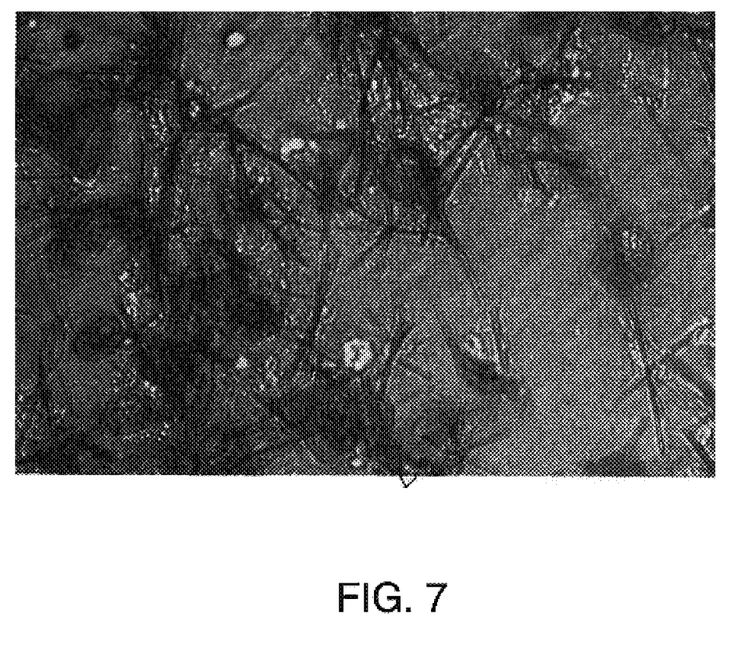
FIG. 7 shows the crystallization of nuclear envelopes (or endoplasmic reticulums or Golgi's complex) of 9 L gliosarcoma cells following treatment with tetrazolium red (TR).

Crystallization of Nuclear Envelopes or Endoplasmic Reticulum of 91 Gliosarcoma Cells Following Treatment with TR 9 L gliosarcoma cancer cells were exposed to TR (50 ug/ml)—a substrate of SDH. The tumor cells (4000) were seeded one day before being treated with TR. As can be seen in FIG. 7, nuclear envelopes and/or endoplasmic reticulum in most cells were frozen by the crystals formed on them.

These kinds of crystals on the cellular structures (described above in Examples 4 through 7) could be inhibited by heating cells in hot water ($>60°$ C.) for more than 30 minutes, or by prior incubation with SDH inhibitor (nitropropionic acid, a typical irreversible SDH inhibitor). The crystallization of organelles, such as centrosome, mitochondrion, or nuclear envelopes (or endoplasmic reticulum), effectively stopped cell proliferation and induced cell death as well. This kind of cell death, which is different from either necrosis or apoptosis, is called cellular-organelle-crystallization-induced-death, "COCID". COCID also refers to the cell death, induced by the crystallization of cytoskeletons as well as the crystallization of the sub-units of cellular organelles and cytoskeletons. COCID further refers to the cell death, induced by the crystallization of proteins and small molecules located on cytoskeletons or the sub-units of cellular organelles and cytoskeletons.

Although the mechanisms are still to be explored, and not wishing to be bound by any particular theory, the inventor believes that the formation of crystals may deactivate and/or freeze the key enzymes/proteins that are located at the crystallizing sites. The formation of crystals may also induce the mechanical damage to the cellular structures such as cell membrane, plasma membrane, organelles, and cytoskeletons. As described above, the cytoskeleton, a complex network of protein filaments traversing the cell cytoplasm, is not simply a passive feature of the cell that provides structural integrity, it is a dynamic structure that is responsible for whole-cell movement, changes in cell shape, and contraction. It provides the machinery to move organelles from one place to another in the cytoplasm. It is recently evidenced that cytoskeleton is a master organizer of the cell's cytoplasm, furnishing binding sites for the specific localization of ribonucleic acids (RNAs) and proteins that were once thought to diffuse freely through the cytoplasm. Cytoskeleton is also responsible for signal transduction. Activities of the cytoskeleton depend mainly on just three principal types of protein assemblies: actin filaments, microtubules, and intermediate filaments. Each type of filament or microtubule is formed from specific association of protein monomers. The dynamic aspects of the cytoskeletal structures arise from accessory proteins that control the length of the assemblies, their position within the cell, and the specific-binding sites along the filaments and microtubules for association with protein complexes, organelles, and the cell membrane. Thus, crystallization of these proteins, and protein filaments may take place. Dynamically, crystallization of microtubules, centrosomes, and other cytoskeletons may interfere with the message (or signal) transmission or cell motility, and consequently make the cells lacking in mitosis motive force. The crystallization of nuclear envelopes may block the duplication of chromatins, and therefore obstruct the formation of daughter cells.

As the formation of crystals is based on the dehydrogenating reaction, and the dehydrogenating enzymes are usually highly expressed in cancer cells, this method therefore has relative high specificity. When used for cancer therapy, crystallizing agent(s) will target tumor cells more selectively, leaving the normal cells greatly protected. Also, the formation of crystals on the cell organelles and cytoskeletons may deactivate or freeze all enzymes located on them, the crystallizing agent might be more effective and logic as compared to any specific enzyme inhibitors either used alone or in combination. Specifically, once the crystals are formed on the cytoskeletons, the affected cells will loose the ability to do any biological or structural modulations against stresses. Therefore, crystallizing agents are particularly useful in sensitizing tumor cells to therapeutic agents and other non-surgical anticancer therapies. The results of the experiments described above, illustrated as only examples, provide strong support.

a) Tumor cells. A low passage number of tumor cells were cultured in different media. For 9 L gliosarcoma tumor cells (isolated from Fischer 344 rats), cells were cultured in Dulbecco's modified Eagle's medium containing 10% fetal calf serum (Gibco, Grand Island, N.Y.), 200 mM L-glutamine, 100 U/ml penicillin, and 0.1 mg/ml streptomycin for 4-5 days. For SHP-77 SCLC, cells were cultured in the same condition without RPIM 1640 added. Cells were washed and resuspended in phosphate buffered saline before use.

b) Infusion of the tumor cells. Subcutaneous infusion of the tumor cells was performed with unanesthetized rats. Phosphate-buffered saline (500 µl) containing $2\times10^5$ 9 L tumor cells was drawn up into a 1 ml syringe. The cells are then infused into the right flank of rats.

c) Drug administrations. Administration of polymer was performed with unanesthetized rats. Before administration, pre-weighed doses of polymer were introduced, using a specifically designed plastic cone, into a sharp cannula. The polymer was then injected into tumor area using a small plunger. The procedure for drug injection was similar to that for tumor cell injection.

d) Preparation of drug containing polymer. Pre-weighed drugs (e.g. NPPA, colchicine and/or Taxol) and lactic acid at a desired ratio were completely dissolved in a given volume of dichloromethane. The drug containing solution was then degassed using a vacuum pump for 5 to 24 hours. The almost dried polymer was harvested for shaping, and then farther dried in an incubator at 10 to 37° C. for approximately 20 to 40 hours. The dried polymer was then sterilized using gamma-irradiation and kept in a dry, cool storage area before using.

e) Statistics. Mean survival time will be analyzed using the Student T test and Log-Rank analysis. P values will be considered significant if smaller than 0.05, very significant if smaller than 0.01.

The foregoing description is considered as illustrative only of the principles of the invention. Since numerous modifications and changes will readily occur to those skilled in the art, it is not desired to limit the invention to the exact construction and process shown as described above. Accordingly, all suitable modifications and equivalents may be resorted to falling within the scope of the invention as defined by the claims which follow.

What is claimed is:

1. A method for inhibiting tumor growth comprising:
   a) administering directly to a tumor site in a mammal an effective amount of an organelle and cytoskeleton crystallizing agent, wherein said crystallizing agent is selected from the group consisting of p-Anisyl Blue Tetrazolium Chloride, p-Anisyl-p-Nitro Blue Tetrazolium Chloride, Thiazolyl blue, 2-2'-Benzothiazolyl-5-styryl-3-(4-phthalhydrazidyl) tetrazolium chloride), Blue tetrazolium chloride, 2-(2'-Benzothiazolyl)-5-styryl-3-(4'-phthalhydrazidyl)-tetrazolium chloride, 5-Cyano-2,3-ditolyl tetrazolium chloride, 1-[4,5-dimethylthiazol-2-yl]-2,5-diphenyltetrazolium bromide, Distyryl nitroblue tetrazolium chloride, (1H)-tetrazole, Iodonitrotetrazolium chloride, Iodo Nitro Tetrazolium Violet Chloride, p-iodo nitrotetrazolium violet, (2-(4-iodophenyl)-3-(4-nitrophenyl)-5-phenyltetrazolium chloride, 2-(p-iodophenyl)-p-nitrophenyl-5-phenyltetrazolium chloride, m-Nitro Blue Tetrazolium Chloride, m-Nitro Neotetrazolium Chloride, 2,2-bis(2-methoxyl-4-nitro-5-sulfophenyl)-2H-tetrazolium-5-carboxanilide, 3-(4,5-dimethylthiazol-2-yl)-5-(3-carboxymethoxyphenyl)-2-(4-sulfophenyl)-2H-tetrazolium salt, tetrazolium bromide, thiazolyl blue tetrazolium bromide, (3→4,5-dimethylthiazol-2-yl-2,5-diphenyltetrazolium bromide), Nitro Blue Monotetrazolium Chloride, p-Nitro Blue Tetrazolium Chloride, (2,2'-dinitrophenyl-5,5'-diphenyl-3,3'-(3,3'-dimethoxy-4,4'-diphenylene ditetrazolium chloride), Neotetrazolium chloride (2,2',5,5'-Tetraphenyl-3,3'(p-diphenylene))-ditetrazolium chloride, Nitrotetrazolium Violet, Thiazolyl blue, tetrazolium blue chloride (3,3'→3,3'-dimethoxy(1,1'-biphenyl)-4,4'-diyl]-bis(2,5-diphenyl-2H-tetrazolium)dichloride), o-Tolyl Tetrazolium Red, sodium 3'-[1-[(phenylamino)-carbonyl]-3,4-tetrazolium]-bis(4-methoxy-6-nitro)benzene-sulfonic acid hydrate, Piperonyl Tetrazolium Blue, p-Tolyl Tetrazolium Red, Thiocarbamyl nitro blue tetrazolium chloride, 2,2'-di-p-nitrophenyl-5,5'-di-p-thiocarbamylphenyl-3,3'[3,3'-dimethoxy-4,4'-biphenylene]-ditetrazolium chloride, Tetranitroblue tetrazolium chloride, 1,3,5-triphenyltetrazolium, Tetrazolium Red, 2,3,5-triphenyltetrazolium chloride, Tetrazolium violet, 2,3,5-Triphenyl-2-H-tetrazolium chloride, 2,5-diphenyl-3-[α-naphthyl]-tetrazolium chloride, 2,5-diphenyl-3-[1-naphthyl]-2H-tetrazolium chloride, Veratryl tetrazolium blue, 4-[3-(4-iodophenyl)-2-(4-nitrophenyl)-2H-5-tetrazolio]-1,3-benzene disulfonate, and 2,2-bis(2-methoxyl-4-notro-5-sulfophenyl)-2H-tetrazolium-5-carboxanilide, and wherein said crystallizing agent forms crystals in an organelle and/or cytoskeleton of tumor cells through a reaction catalyzed by cellular enzymes; and,
   b) administering to said mammal an effective amount of a chemotherapeutic agent selected from the group consisting of acalacinomycin, alitretinoin, allopurinol, altretamine, anastrozole, arsenic trioxide, asparaginase, busulfan, calusterone, camptothecin, capecitabine, carmofur, cladribine, dacarbazine, dexrazoxane, docetaxel, doxifloridine, doxorubicin, dromostanolone, epirubicin, estramustine, etoposide, exemestane, floxuridine, fludarabine, fluorouracil, fulvestrant, gemcitabine, homoharringtonine, hydroxycamptothecin, hydroxyurea, irinotecan, letrozole, levamisole, mesna, mitotane, mitoxantrone, oxaliplatin, paclitaxel, pipobroman, pirarubicin, Sarmustine, semustine, tamoxifen, tegafururacil, temozotomide, teniposide, testolactone, thioguanine, thiotepa, topotecan, valrubicin, vinblastine, vincristine, vindesine, and vinorelbine.

2. The method for inhibiting tumor growth of claim 1, wherein the organelle and cytoskeleton crystallizing agent and the chemotherapeutic agent are administered in a biodegradable polymer.

3. The method for inhibiting tumor growth of claim 2, wherein the biodegradable polymer is a polymer comprising polylactic acid.

4. A method for inhibiting tumor growth comprising administering directly to a tumor site in a mammal an effective amount of an organelle and cytoskeleton crystallizing agent and a chemotherapeutic agent in a biodegradable polymer, wherein said crystallizing agent is selected from the group consisting of p-Anisyl Blue Tetrazolium Chloride, p-Anisyl-p-Nitro Blue Tetrazolium Chloride, Thiazolyl blue, 2-2'-Benzothiazolyl-5-styryl-3-(4'-phthalhydrazidyl)tetrazolium chloride), Blue tetrazolium chloride, 2-(2'-Benzothiazolyl)-5-styryl-3-(4'-phthalhydrazidyl)-tetrazolium chloride, 5-Cyano-2,3-ditolyl tetrazolium chloride, 1-[4,5-dimethylthiazol-2-yl]-2,5-diphenyltetrazolium bromide, Distyryl nitroblue tetrazolium chloride, (1H)-tetrazole, Iodonitrotetrazolium chloride, Iodo Nitro Tetrazolium Violet Chloride, p-iodo nitrotetrazolium violet, (2-(4-iodophenyl)-3-(4-nitrophenyl)-5-phenyltetrazolium chloride, 2-(p-iodophenyl)-p-nitrophenyl-5-phenyltetrazolium chloride, m-Nitro Blue Tetrazolium Chloride, m-Nitro Neotetrazolium Chloride, 2,2-bis(2-methoxyl-4-nitro-5-sulfophenyl)-2H-tetrazolium-5-carboxanilide, 3-(4,5-dimethylthiazol-2-yl)-5-(3-carboxymethoxyphenyl)-2-(4-sulfophenyl)-2H-tetrazolium salt, tetrazolium bromide, thiazolyl blue tetrazolium bromide, (3→4,5-dimethylthiazol-2-yl-2,5-diphenyltetrazolium bromide), Nitro Blue Monotetrazolium Chloride, p-Nitro Blue Tetrazolium Chloride, (2,2'-di-nitrophenyl-5,5'-diphenyl-3,3'-(3,3'-dimethoxy-4,4'-diphenylene ditetrazolium chloride), Neotetrazolium chloride (2,2',5,5'-Tetraphenyl-3,3'(p-diphenylene))-ditetrazolium chloride, Nitrotetrazolium Violet, Thiazolyl blue, tetrazolium blue chloride (3,3'→3,3'-dimethoxy(1,1'-biphenyl)-4,4'-diyl]-bis(2,5-diphenyl-2H-tetrazolium)dichloride), o-Tolyl Tetrazolium Red, sodium 3'-[1-[(phenylamino)-carbonyl]-3,4-tetrazolium]-bis(4-methoxy-6-nitro)benzene-sulfonic acid hydrate, Piperonyl Tetrazolium Blue, p-Tolyl Tetrazolium Red, Thiocarbamyl nitro blue tetrazolium chloride, 2,2'-di-p-nitrophenyl-5,5'-di-p-thiocarbamylphenyl-3,3'[3,3'-dimethoxy-4,4'-biphenylene]-ditetrazolium chloride, Tetranitroblue tetrazolium chloride, 1,3,5-triphenyltetrazolium, Tetrazolium Red, 2,3,5-triphenyltetrazolium chloride, Tetrazolium violet, 2,3,5-Triphenyl-2-H-tetrazolium chloride, 2,5-diphenyl-3-[α-naphthyl]-tetrazolium chloride, 2,5-diphenyl-3-[1-naphthyl]-2H-tetrazolium chloride, Veratryl tetrazolium blue, 4-[3-(4-iodophenyl)-2-(4-nitrophenyl)-2H-5-tetrazolio]-1,3-benzene disulfonate, and 2,2-bis(2-methoxyl-4-notro-5-sulfophenyl)-2H-tetrazolium-5-carboxanilide, wherein said crystallizing agent forms crystals in an organelle and/or cytoskeleton of tumor cells through a reaction catalyzed by cellular enzymes, and wherein the chemotherapeutic agent is selected from the group consisting of acalacinomycin, alitretinoin, allopurinol, altretamine, anastrozole, arsenic trioxide, asparaginase, busulfan, calusterone, camptothecin, capecitabine, carmofur, cladribine, dacarbazine, dexrazoxane, docetaxel, doxifloridine, doxorubicin, dromostanolone, epirubicin, estramustine, etoposide, exemestane, floxuridine, fludarabine, fluorouracil, fulvestrant, gemcitabine, homoharringtonine, hydroxycamptothecin, hydroxyurea, irinotecan, letrozole, levamisole, mesna, mitotane, mitoxantrone, oxaliplatin, paclitaxel, pipobroman, pirarubicin, sarmustine, semustine, tamoxifen, tegafur-uracil, temozotomide, teniposide, testolactone, thioguanine, thiotepa, topotecan, valrubicin, vinblastine, vincristine, vindesine, and vinorelbine.

5. The method for inhibiting tumor growth of claim 4, wherein the biodegradable polymer is a polymer comprising polylactic acid.

6. A pharmaceutical composition for inhibiting tumor growth comprising:

a therapeutically effective amount of an organelle and cytoskeleton crystallizing agent selected from the group consisting of p-Anisyl Blue Tetrazolium Chloride, p-Anisyl-p-Nitro Blue Tetrazolium Chloride, Thiazolyl blue, 2-2'-Benzothiazolyl-5-styryl-3-(4'-phthalhydrazidyl)tetrazolium chloride, Blue tetrazolium chloride, 2-(2'-Benzo thiazolyl)-5-styryl-3-(4'-phthalhydrazidyl)-tetrazolium chloride, (5-Cyano-2,3-ditolyl tetrazolium chloride), Distyryl nitroblue tetrazolium chloride; (1H)-tetrazole, Iodonitrotetrazolium chloride, Iodo Nitro Tetrazolium Violet Chloride, p-iodo nitrotetrazolium violet, (2-(4-iodophenyl)-3-(4-nitrophenyl)-5-phenyltetrazolium chloride, 2-(p-iodophenyl)-p-nitrophenyl-5-phenyltetrazolium chloride, m-Nitro Neotetrazolium Chloride, 2,2-bis(2-methoxyl-4-nitro-5-sulfophenyl)-2H-tetrazolium-5-carboxanilide, 3-(4,5-dimethylthiazol-2-yl)-5-(3-carboxymethoxyphenyl)-2-(4-sulfophenyl)-2H-tetrazolium salt, Nitro Blue Monotetrazolium Chloride, p-Nitro Blue Tetrazolium Chloride, Nitro blue tetrazolium chloride, (2,2'-di-nitrophenyl-5,5'-diphenyl-3,3'-(3,3'-dimethoxy-4,4'-diphenylene)ditetrazolium chloride), Neotetrazolium chloride (2,2',5,5'-Tetraphenyl-3,3'(p-diphenylene)-ditetrazolium chloride, Nitrotetrazolium Violet; Thiazolyl blue, tetrazolium blue chloride (3,3'→3,3'-dimethoxy(1,1'-biphenyl)-4,4'-diyl]-bis(2,5-diphenyl-2H-tetrazolium)dichloride), o-Tolyl Tetrazolium Red, sodium 3'-[1-[(phenylamino)-carbonyl]-3,4-tetrazolium]-bis(4-methoxy-6-nitro)benzene-sulfonic acid hydrate, Piperonyl Tetrazolium Blue, p-Tolyl Tetrazolium Red, Thiocarbamyl nitro blue tetrazolium chloride, (2,2'-di-p-nitrophenyl-5,5'-di-p-thiocarbamylphenyl-3,3'[3,3'-dimethoxy-4,4'-biphenylene]-ditetrazolium chloride, Tetranitroblue tetrazolium chloride, 1,3,5-triphenyltetrazolium, Tetrazolium Red, 2,3,5-triphenyltetrazolium chloride), Tetrazolium violet, 2,3,5-Triphenyl-2-H-tetrazolium chloride, 2,5-diphenyl-3-[α-naphthyl]-tetrazolium chloride, 2,5-diphenyl-3-[1-naphthyl]-2H-tetrazolium chloride, Veratryl tetrazolium blue, 4-[3-(4-iodophenyl)-2-(4-nitrophenyl)-2H-5-tetrazolio]-1,3-benzene disulfonate, 2,2-bis(2-methoxy]-4-notro-5-sulfophenyl)-2H-tetrazolium-5-carboxanilide, and combinations thereof, a chemotherapeutic agent selected from the group consisting of acalacinomycin, alitretinoin, allopurinol, altretamine, anastrozole, arsenic trioxide, asparaginase, busulfan, calusterone, camptothecin, capecitabine, carmofur, cladribine, dacarbazine, dexrazoxane, docetaxel, doxifloridine, doxorubicin, dromostanolone, epirubicin, estramustine, etoposide, exemestane, floxuridine, fludarabine, fluorouracil, fulvestrant, gemcitabine, homoharringtonine, hydroxycamptothecin, hydroxyurea, irinotecan, letrozole, levamisole, mesna, mitotane, mitoxantrone, oxaliplatin, paclitaxel, pipobroman, pirarubicin, sarmustine, semustine, tamoxifen, tegafur-uracil, temozotomide, teniposide, testolactone, thioguanine, thiotepa, topotecan, valrubicin, vinblastine, vincristine, vindesine, and vinorelbine, and a pharmaceutically-acceptable carrier comprising a biodegradable polymer.

7. The pharmaceutical composition of claim 6, wherein the organelle and cytoskeleton crystallizing agent is selected from the group consisting of tetrazolium red and tetrazolium violet.

8. The pharmaceutical composition of claim 6, wherein the biodegradable polymer is a polymer comprising polylactic acid.

* * * * *